United States Patent [19]

Thomissen

[11] Patent Number: 5,571,913

[45] Date of Patent: Nov. 5, 1996

[54] PROCESS FOR PREPARING A LACTAM

[75] Inventor: Petrus J. H. Thomissen, Lanaken, Belgium

[73] Assignee: DSM N.V., Heerlen, Netherlands

[21] Appl. No.: 293,098

[22] Filed: Aug. 19, 1994

[30] Foreign Application Priority Data

Aug. 20, 1993 [BE] Belgium ................. 09300848

[51] Int. Cl.$^6$ ................... C07D 201/02; C07D 201/04
[52] U.S. Cl. ............... 540/532; 540/200; 540/464; 546/243; 548/552
[58] Field of Search ................. 540/464, 532, 540/200; 546/243; 548/552

[56] References Cited

U.S. PATENT DOCUMENTS 3,836,525  9/1974  Masaki et al. ............... 260/239.3 A
3,944,542  3/1976  de Rooij et al. ............. 260/239.3

FOREIGN PATENT DOCUMENTS 1301646  8/1970  United Kingdom .
1342550  1/1974  United Kingdom .

*Primary Examiner*—Cecilia Tsang
*Assistant Examiner*—King Lit Wong
*Attorney, Agent, or Firm*—Cushman Darby & Cushman L.L.P.

[57] ABSTRACT

The invention relates to a process for preparing a lactam from an alicyclic ketoxime in the presence of a lactim-O-sulphonic acid and a solvent, the reaction being carried out in the presence of an acid cation exchanger. The invention relates in particular to a process in which the alicyclic ketoxime is represented by the following general formula:

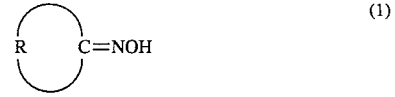

(1)

where R is a linear or branched alkylidene group containing from 3 to 20 carbon atoms.

11 Claims, 1 Drawing Sheet

PROCESS FOR PREPARING A LACTAM

FIELD OF THE INVENTION

The invention relates to a process for preparing a lactam from an alicyclic ketoxime in the presence of a lactim-O-sulphonic acid and a solvent.

BACKGROUND OF THE INVENTION

Such a process is known from GB-A-1301646. This publication describes a process in which in a first reaction step a cyclohexanone oxime/tin (IV) chloride complex in the presence of ε-caprolactim-O-sulphonic acid is converted to an ε-caprolactam/tin chloride complex. Subsequently, the complex so formed is separated and in a second reaction step contacted with cyclohexanone oxime, in which ε-caprolactam and a cyclohexanone oxime/tin chloride complex is formed. The ε-caprolactam is recovered and the cyclohexanone oxime/tin chloride complex is recirculated to the first reaction step. The net result of all these reactions is that cyclohexanone oxim (alicyclic ketoximes) are converted to free ε-caprolactam (lactam) in the presence of a cyclohexanone oxime/tin chloride complex (tin chloride complex).

A disadvantage of this known process is that relatively many process steps are needed for preparing lactam. After each reaction step the desired product is separated off by, for instance, crystallization, which is not easy to accomplish for this group of reagents. In addition, the process is complicated by the introduction of tin(IV)chloride, a corrosive, moisture-sensitive reagent.

SUMMARY AND OBJECTS IN THE INVENTION

The object of the invention is a simple process involving relatively few process steps for the preparation of a lactam starting from an alicyclic ketoxime in the presence of lactim-O-sulphonic acid.

This object is achieved in that the reaction is carried out in the presence of an acid cation exchanger.

It has been found that, if the lactam is prepared by the process according to the invention, lactam can be prepared in a single process step starting from an alicyclic ketoxime (hereinafter shortly oxime). As a further advantage, the use of tin chloride and/or tin chloride complexes can be avoided. A third advantage is that the selectivity for lactam is higher than that attained in the process according to GB-A-1301646.

Figure 1:
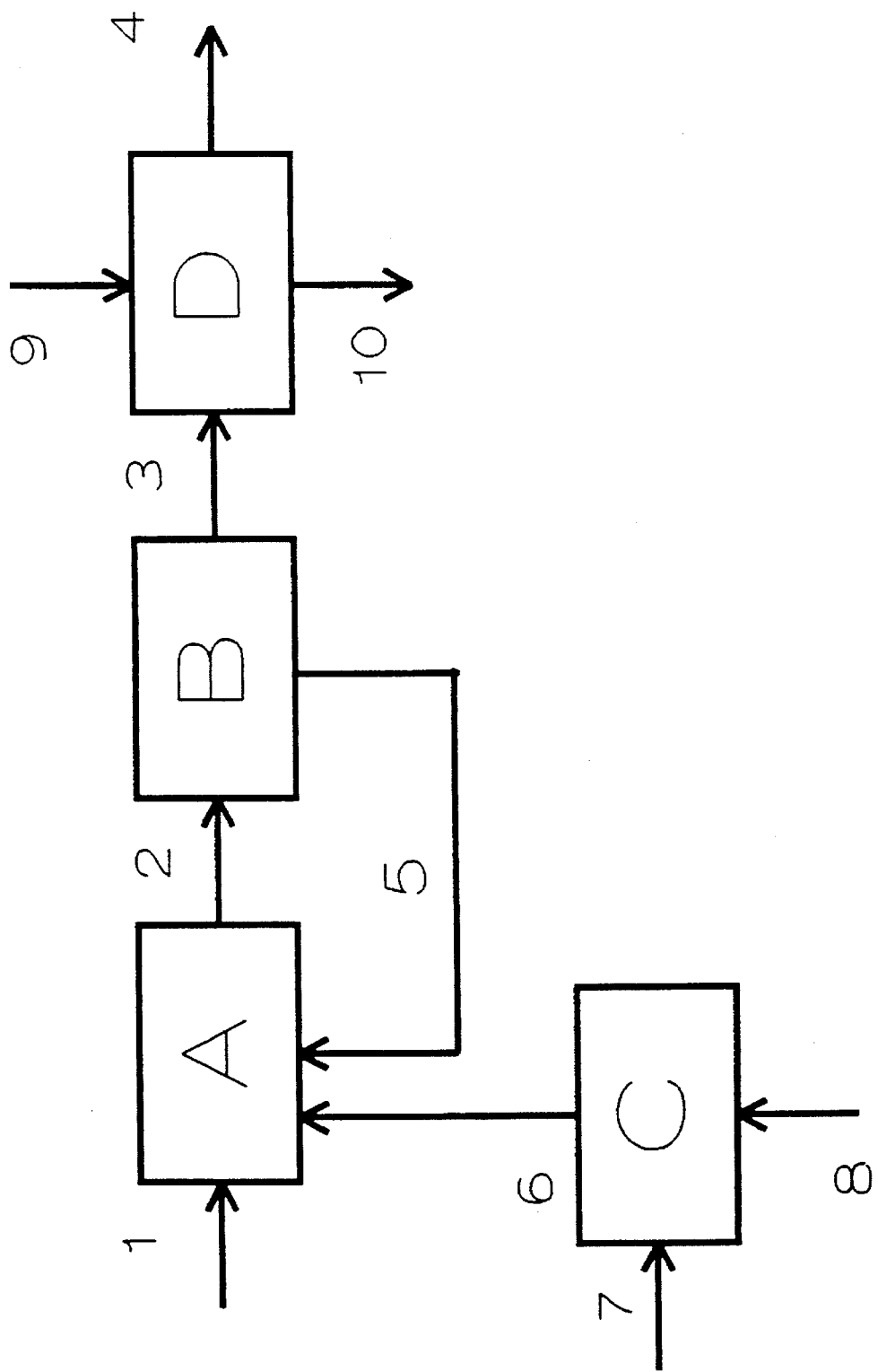
FIG. 1 presents a schematic of an embodiment of the process according to the present invention.

The process according to the invention obviates the use of oleum for the preparation of lactam starting from an aliphatic ketoxime. This is advantageous because oleum is very corrosive and therefore needs a complicated handling. The rearrangement of an aliphatic ketoxime to lactam in oleum, also known as the Beckmann rearrangement, is a process commonly used in practice for the preparation of lactams, in particular for the preparation of ε-caprolactam. In such a process the lactam is recovered from the reaction mixture by neutralizing with ammonia water and then extracting the lactam from the ammonium-sulphate-containing solution obtained. A disadvantage of this process is that in the production of, for instance, ε-caprolactam, 1.7–1.9 tonnes of $(NH_4)_2SO_4$ per tonne of lactam is prepared as by-product. Since ammonium sulphate is increasingly difficult to sell and causes environmental problems, such by-production is considered undesirable, so that efforts have been made for quite some time to find ways of rearranging alicyclic ketoximes to lactams without by-production of ammonium sulphate. By applying the process according to the invention, it is possible to prepare lactam with virtually no by-production of $(NH_4)_2SO_4$.

The alicyclic ketoxime is represented by the following general formula:

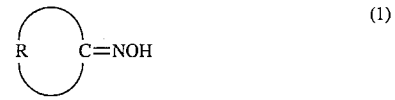

where R is a linear or branched alkylene group containing from 3 to 20 carbon atoms.

The lactim-O-sulphonic acid is represented by the following general formula:

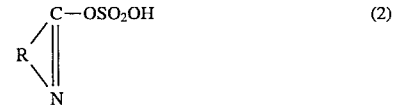

where R is equal to R in formula (1).

Preferably, R is a linear pentamethylene group inasmuch as the corresponding lactam is ε-caprolactam, which ε-caprolactam is the raw material for Nylon-6, or a linear heptamethylene group or a linear undecamethylene group. Examples of suitable lactim-O-sulphonic acids are caprolactim-O-sulphonic acid (R=pentamethylene group), capryllactim-O-sulphonic acid (R=heptamethylene group), undecanolactim-O-sulphonic acid (R=decamethylene group), laurolactim-O-sulphonic acid (R=undecamethylene group), methylcaprolactim-O-sulphonic acid (R=methyl substituted pentamethylene group) and ethylvalerolactim-O-sulphonic acid (R=ethyl substituted tetramethylene group).

The lactim-O-sulphonic acid may be prepared by a variety of processes known to one skilled in the art. A possible process involves first preparing the oxime-O-sulphonic acid from oxime and dioxane. $SO_3$ as described in J. Org. Chem. 36, 2159, 1971 and Ind. Eng. Chem. Prod. Res. Develop., 7, 189 (1968) and subsequently converting the oxime-O-sulphonic acid at, for instance, 44° C., to the corresponding lactim-O-sulphonic acid by rearrangement as described in Bull of the Chem. Soc. Jpn., Vol. 46, 3168–3173 (1973). Lactim-O-sulphonic acid can also be prepared by dissolving $SO_3$ in a (virtually) water-free inert solvent, for example such as 1,2-dichloroethane and gradually adding a mixture of lactam in an identical solvent to this mixture at a low temperature, for instance 10° C.

In general, the reaction is effected under (virtually) water-free conditions in a solvent that is inert and liquid under the reaction conditions according to the process according to the invention and in which the lactim-O-sulphonic acid and oxime readily dissolve. Examples of suitable solvents are liquid $SO_2$ and halogenated hydrocarbons having from 1 to 10 carbon atoms, for example 1,2-dichloroethane. The suitability of the solvent can readily be established by one skilled in the art. Known solvents for rearrangement reactions under the influence of an ion exchanger as described in GB-A-1342550, such as dimethylsulphoxide (DMSO) or $CH_3CN$ appear to be less suitable.

As a rule, the temperature is between −30° C. and 50° C. and preferably is higher than −5° C. and lower than 30° C.

The pressure is a less critical parameter and will depend on, inter alia, the solvent applied. As a rule, the pressure is between 0.01 and 2 MPa.

Suitable acid cation exchangers may be ion exchangers having an inorganic or organic structure that are capable of donating a hydrogen atom and that do not bind the lactim-O-sulphonic acid or the formed lactam too strongly. Cation exchangers having —$SO_3H$ groups, for instance, have been found to be particularly suitable for this purpose. These —$SO_3H$ groups are preferably linked to a benzene ring, whether or not via a $C_1$–$C_4$ alkyl group, the benzene ring being or not being directly linked to, or forming a part of, the organic or inorganic structure of the cation exchanger. A sulphonated benzene ring may or may not be further substituted with electronegative groups such as halides (-Cl, -Br, -F, -I), a nitro group or an extra —$SO_3H$ group. As a rule, the capacity of the ion exchanger according to the invention is between 0.1 meq $H^+$ and 6 meq $H^+$ per gram of dry ion exchanger. Examples of suitable ion exchangers having an organic structure are sulphonated polymers for example polyacrylate, poly(styrene-co-divinylbenzene) and poly(naphtalene-co-divinylbenzene) resin. Examples of suitable sulphonated poly(styrene-co-divinylbenzene) resins are supplied by, for example, Rohm and Haas under the tradename Amberlyst 15, by Bayer under the tradename Lewatit, by Dow under the tradename DOWEX, by Mitsubishi under the tradename Diaion and by Purolex with their CT type. Another suitable sulphonated polymer is Nafion (DuPont) (=copolymer of tetrafluoroethylene and perfluoro-3,6-dioxa- 4-methyl-7-octenesulphonylfluoride). An example of a sulphonated poly(styrene-co-divinylbezene) resin which is additionally substituted with chloride atoms is Amberlyst 17 (Rohm & Haas). An example of a bisulphonated poly(styrene-co-divinylbenzene) resin is Amberlyst 35 (Rohm & Haas).

Examples of cation exchangers having an inorganic structure are: heterogeneous carbon and heterogeneous metal oxides having free OH groups such as $SiO_2$, $Al_2O_3$, ZnO, $TiO_2$ and MgO that are chemically bonded to, for instance, the sulphonated benzene ring (directly or, for instance, via an alkyl group). An example of an inorganic carrier in combination with sulphonated benzene rings is silica which is linked to a sulphonated benzene ring via a silane alkyl group:

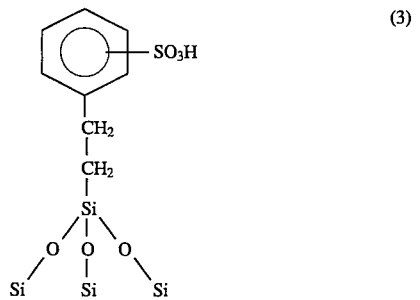

(3)

As a rule, the oxime concentration in the reaction mixture for the reaction is between 0.1 and 25 wt. %. Preferably, this concentration is lower than 15%. Preferably, this concentration is higher than 1 wt. %.

As a rule, the ratio between the initial amount of oxime (moles) and the number of ion exchanger equivalents is between 1:20 and 2:1, preferably between 1:10 and 1.5:1.

As a rule, the process according to the invention is conducted with excess lactim-O-sulphonic acid relative to the oxime (moles). In the case of a deficiency of lactim-O-sulphonic acid, the selectivity will be low as many by-products will be formed. Preferably, the molar ratio between lactim-O-sulphonic acid and oxime in the initial mixture is higher than 2:1.

The process according to the invention may be carried out batch-wise or continuously.

Following the reaction, which yields a reaction mixture high in lactam, the lactam may be recovered by any suitable separation technique known to one skilled in the art. The remaining lactim-O-sulphonic acid and the solvent may be returned to the reaction with advantage. Suitable separation techniques are, for instance, crystallization and extraction.

During the aforementioned lactam recovery a small proportion of the lactim-O-sulphonic acid may remain behind along with the lactam that has been separated out. As a rule, the ratio of the remaining lactim-O-sulphonic acid and the lactim-O-sulphonic acid recirculated to the reaction is between 1:60 and 1:20. The lactim-O-sulphonic acid may be separated out of the lactam using known techniques. An obvious technique is neutralization with a sodium hydroxide solution or ammonia water. It is true that this yields sodium sulphate and ammonium sulphate, respectively. However, the amount of sulphate salt per tonne of lactam is significantly less (at least about 20 times less) than the amount of sulphate salt prepared as a by-product in the process for the preparation of lactam in oleum mentioned earlier. In order to make good the loss of lactim-O-sulphonic acid, extra lactim-O-sulphonic acid will need to be added to the reaction. This make-up lactim-O-sulphonic acid may, for instance, be prepared in situ starting from lactam and $SO_3$ as mentioned earlier.

A possible embodiment of the process according to the invention is shown in FIG. 1. This includes the addition of extra lactim-O-sulphonic acid. FIG. 1 will be explained for the preparation of ε-caprolactam. Some solvent recirculation streams have been omitted in Figure in the interest of clarity.

In FIG. 1, reactor A, which is filled with an acid cation exchanger, receives cyclohexanone oxime via stream 1 and ε-caprolactim-O-sulphonic acid and the solvent via stream 6. The mixture of solvent, unconverted cyclohexanone oxime, if any, ε-caprolactim-O-sulphonic acid and ε-caprolactam goes to separation step B via line 2. In separation step B, the unconverted cyclohexanone oxime, if any, and the ε-caprolactim-O-sulphonic acid are separated from the ε-caprolactam. For example by first evaporating a large part of the solvent and mixing the residue with an aromatic solvent, for example, benzene or preferably toluene. The ε-caprolactim-O-sulphonic acid precipitates and can be separated and recycled to reactor A through 5. Via line 3 the ε-caprolactam rich mixture is led to purification step D where any residual lactim-O-sulphonic acid is reacted with a base (added via line 9) to form ε-caprolactam and the corresponding sulphate salt. Via line 10 the sulphate salt is removed. ε-caprolactam is discharged via line 4. Unconverted cyclohexanone oxime, if any, ε-caprolactim-O-sulphonic acid and solvent are recirculated to reactor A via line 5. In reactor C an amount of ε-caprolactim-O-sulphonic acid is prepared starting from $SO_3$ (via line 7) and ε-caprolactam (via line 8). This amount of ε-caprolactim-O-sulphonic acid is added to reactor A via line 6.

The invention will be elucidated by means of the following non-limiting examples, where:

$$\text{Oxime conversion (\%)} = \frac{\text{moles of reacted oxime}}{\text{moles of original oxime}} * 100\%$$

$$\text{Lactam selectivity (\%)} = \frac{\text{moles of lactam obtained}}{\text{moles of reacted oxime}} * 100\%$$

EXAMPLE I

Lactim-O-sulphonic acid was prepared by dissolving 8.0 g of $SO_3$ freshly distilled from 65-% oleum (65% $SO_3$ and 35% H₂SO₄), in 15 ml of dry 1,2-dichloroethane to which a solution of 11.3 g of caprolactam in 10 ml of 1,2-dichloroethane was added drop-wise at 10° C. while stirring intensively. When the solubility concentration was exceeded, the caprolactim-O-sulphonic acid crystallized. After washing with 1,2-dichlororethane, the crystals were dried with nitrogen and stored with exclusion of moisture. The 1,2-dichloroethane was dried before use by intimate mixing with a molecular sieve with a pore size of 300 nm.

Table 1.

COMPARATIVE EXAMPLE A

Example II was repeated using 115 ml of DCE, 2.3 g of cyclohexanone oxime and 3.9 g of ε-caprolactim-O-sulphonic acid in the absence of a cation exchanger. The results are given in Table 1.

TABLE 1

| Examples I–VI and Experiment A | oxime/acid[1] ratio | oxime/LS[2] molar ratio | % conversion oxime | % selectivity lactam | remainder |
|---|---|---|---|---|---|
| II  ox + LS + A15[3] | 0.73 | 1.0 | 36.1 | 97.4 | 2.6 |
| III ox + LS + A15 | 0.73 | 0.34 | 100.0 | 100.0 | 0.0 |
| IV ox + LS + A15 | 0.19 | 1.0 | 16.9 | 86.9 | 13.1 |
| V  ox + LS + A17 | 0.38 | 1.0 | 30.9 | 92.8 | 7.2 |
| VI ox + LS + A17 | 1.23 | 1.0 | 47.1 | 91.1 | 8.9 |
| A  ox + LS | — | 1.0 | 86.2 | 26.1 | 73.9 |

[1] oxime/acid = mol oxime cation exchanger equivalents
[2] LS = lactim-OSO₃H
[3] A15 = Amberlyst 15
A17 = Amberlyst 17

EXAMPLE II

In a stirred glass reactor with a capacity of 150 ml, 3.9 g of caprolactim-O-sulphonic acid prepared in Example I (lactim-OSO₃H) was dissolved in 115 ml of 1,2-dichloroethane. On cooling to −7° C., a solution of 2.3 g of cyclohexanone oxime in 40 ml of 1,2-dichloroethane and 6.7 g of dry Amberlyst 15 (a monosulfonated ionexchanger) were added. The oxime/lactim OSO₃H molar ratio was 1. Subsequently, the reaction mixture was stirred for 2 hours at a temperature of −7° C. The reaction mixture was neutralized in 2 hours at room temperature using a saturated NaHCO₃/H₂O solution and the mixture was then extracted 4 times using 100 ml of chloroform. The results were obtained by GC analysis and are given in Table 1.

EXAMPLE III

Example II was repeated using 6.7 g of Amberlyst 15, 300 ml of 1,2-dichloroethane (DCE), 2.3 g of cyclohexanone oxime and 11.5 g of ε-caprolactim-O-sulphonic acid. The results are given in Table 1.

EXAMPLE IV

Example II was repeated using 25.9 g of Amberlyst 15, 182 ml of DCE, 2.3 g of cyclohexanone oxime and 3.9 g of ε-caprolactim-O-sulphonic acid. The results are given in Table 1.

EXAMPLE V

Example II was repeated using 13.6 g of Amberlyst 17, 90 ml of DCE, 2.3 g of cyclohexanone oxime and 3.9 g of ε-caprolactim-O-sulphonic acid. The results are given in Table 1.

EXAMPLE VI

Example II was repeated using 4.2 g of Amberlyst 17, 65 ml of DCE, 2.3 g of cyclohexanone oxime and 3.9 g of ε-caprolactim-O-sulphonic acid. The results are given in Table 1.

I claim:
1. Process for preparing a lactam from an alicyclic ketoxime in the presence of a lactim-O-sulphonic acid and a solvent, characterized in that the reaction is carried out essentially Lewis acid free in the presence of an acid cation exchanger, and wherein a molar excess of lactim-O-sulphonic acid is used relative to said alicyclic ketoxime.

2. Process according to claim 1 characterized in that the alicyclic ketoxime is represented by the following general formula:

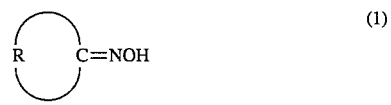

where R is a linear or branched alkylene group containing from 3 to 20 carbon atoms.

3. Process according to claim 2 characterized in that R is a linear alkylene group having 5, 7 or 11 carbon atoms.

4. Process according to claim 1 characterized in that the temperature lies between −30° and 50° C.

5. Process according to claim 1 characterized in that the acid ion exchanger contains —SO₃H groups.

6. Process according to claim 1 characterized in that the oxime concentration in the reaction mixture (exclusive of the ion exchanger) is between 0.1 and 25 wt. %.

7. Process according to claim 1 characterized in that the ratio between the initial amounts of alicyclic ketoxime (moles) and ion exchanger (equivalents) lies between 1:10 and 1.5:1.

8. An oleum-free and essentially water-free process for preparing a lactam from an alicyclic ketoxime in the presence of a lactim-O-sulphonic acid, an inert solvent, and an acid cation exchanger having a number of ion equivalents and having —SO₃H groups, wherein said process is effected essentially Lewis acid free at a temperature between about −30° C. and about 50° C., a molar excess of lactim-O-sulphonic acid is used relative to said alicyclic ketoxime, and the ratio of the initial amount of said alicyclic ketoxime present to the number of ion equivalents present is between 1:20 and 2:1, and wherein said alicyclic ketoxime is represented by the formula

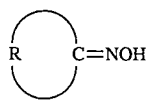 (1)

in which R represents a linear or branched 3 to 20 carbon atom alkylene group, and said lactim-O-sulphonic acid is represented by the formula

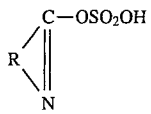 (2)

in which R represents a linear or branched alkylene group.

9. A process for preparing a lactam comprising conducting an essentially Lewis acid free reaction between an alicyclic ketoxime and a caprolactim-O-sulphonic acid with a molar excess of said caprolactim-O-sulphonic acid relative to said alicyclic ketoxime in the presence of a solvent and an acid cation exchanger.

10. A process according to claim 9, wherein the molar amount of said caprolactim-O-sulphonic acid relative to said alicyclic ketoxime is higher than 2:1.

11. Process according to claim 9 characterized in that after the reaction the lactam is separated out and the caprolactim-O-sulphonic acid and the solvent are reused in the preparation of the lactam.

* * * * *